US010570386B2

(12) United States Patent
Wan et al.

(10) Patent No.: US 10,570,386 B2
(45) Date of Patent: Feb. 25, 2020

(54) PCR-BASED METHOD FOR GENERATING MULTISITE SATURATION MUTAGENIC DNA LIBRARIES

(71) Applicant: RANOMICS INC., Toronto (CA)

(72) Inventors: Leo Wan, Richmond Hill (CA); Christina Yeh, Toronto (CA)

(73) Assignee: RANOMICS INC., Toronto (CA)

( * ) Notice: Subject to any disclaimer, the term of this patent is extended or adjusted under 35 U.S.C. 154(b) by 0 days.

(21) Appl. No.: 16/337,461

(22) PCT Filed: Sep. 27, 2017

(86) PCT No.: PCT/CA2017/051141
§ 371 (c)(1),
(2) Date: Mar. 28, 2019

(87) PCT Pub. No.: WO2018/064752
PCT Pub. Date: Apr. 12, 2018

(65) Prior Publication Data
US 2019/0382754 A1    Dec. 19, 2019

(30) Foreign Application Priority Data
Oct. 7, 2016 (CA) .................................... 2944638

(51) Int. Cl.
*C12N 15/10* (2006.01)
*C40B 50/06* (2006.01)

(52) U.S. Cl.
CPC ..... *C12N 15/1031* (2013.01); *C12N 15/1037* (2013.01); *C12N 15/1068* (2013.01); *C40B 50/06* (2013.01)

(58) Field of Classification Search
None
See application file for complete search history.

(56) References Cited

U.S. PATENT DOCUMENTS

2016/0017410 A1    1/2016  Shendure et al.

OTHER PUBLICATIONS

Dennig et al., "OmniChange: the sequence independent method for simultaneous site-saturations of five codons." PLOS One, Oct. 19, 2011, vol. 6(10); e26222, pp. 1-9, ISSN 1932-6203.

Mingo et al., "One-tube-only standardized site-directed mutagenesis: an alternative approach to generate amino acid substitution collections". PLOS One, Aug. 22, 2016 (Aug. 22, 2016), vol. 11(8): 30160972, pp. 1-15, ISSN 1932-6203 [online] [retrieved on Dec. 11, 2017 (Dec. 11, 2017)].

Wang et al., "PCR-based strategy for construction of multi-site saturation mutagenic expression library". Journal of Microbiological Methods, Sep. 11, 2007 (Sep. 11, 2007), vol. 71, No. 3, pp. 225-230, ISSN 0167-7012 [online] [retrieved on Dec. 11, 2017 (Dec. 11, 2017)].

(Continued)

*Primary Examiner* — Kaijiang Zhang
(74) *Attorney, Agent, or Firm* — Jenkins, Wilson, Taylor & Hunt, P.A.

(57) ABSTRACT

Disclosed herein is a novel method for multisite saturation mutagenesis. Provided in the instant disclosure is a means of generating genetic diversity at each desired codon position within the coding sequence of a gene using a multi-oligo-nucleotide primer pool and Gibson assembly approach where a mutant DNA library can be cloned into a target vector.

31 Claims, 8 Drawing Sheets
Specification includes a Sequence Listing.

A

(56) References Cited

OTHER PUBLICATIONS

Zhang et al., "An improved dual-tube megaprimer approach for multi-site saturation mutagenesis". World Journal of Microbiology and Biotechnology, Dec. 7, 2012, vol. 29, pp. 667-672, ISSN 095903993.
Notification of Transmittal of International Search Report and Written Opinion of the International Searching Authority for International Patent Application SN: PCT/CA2017/051141, dated Jan. 16, 2018. (1 page).
International Search Report for International Patent Application SN: PCT/CA2017/051141, dated Jan. 16, 2018. (4 pages).
Written Opinion of the International Searching Authority for International Patent Application SN: PCT/CA2017/051141, dated Jan. 16, 2018. (5 pages).

Figure 5

PCR-BASED METHOD FOR GENERATING MULTISITE SATURATION MUTAGENIC DNA LIBRARIES

RELATED APPLICATION

The present application is an International Patent Application which claims benefit of priority to Canadian Patent Application serial number 2,944,638, entitled "PCR-BASED METHOD FOR GENERATING MULTISITE SATURATION MUTAGENIC DNA LIBRARIES" filed Oct. 7, 2016, the disclosure of which is herein incorporated by reference.

TECHNICAL FIELD

The present disclosure relates to technique for producing a multi-site saturation mutagenic DNA library.

SEQUENCE LISTING

Incorporated herein by reference is a sequence listing with the filename 3206-6 PCT-US_ST25, created Aug. 12, 2019, having a text file size of 3,318 bytes.

BACKGROUND

Molecular cloning is an essential toolset in the study of genetic material in laboratory settings. Through the usage of recombinant polymerases, restriction enzymes and ligases, genetic material can be isolated, amplified and inserted into DNA vectors for downstream functional characterization. In addition to isolating and studying naturally existing genetic material, synthetic recombinant DNA can be created and characterized by incorporating synthetic oligonucleotides into a molecular cloning workflow.

Briefly, at any given position in any gene, there are four possible nucleotides: adenine (A), guanine (G), cytosine (C) and thymine (T). Triplets of these nucleotides in different combinations are known as codons. Each codon in turn encodes for one of the twenty amino acids required for protein synthesis. There may be more than one triplet combination of nucleotides which encode for any given amino acid. Therefore, alteration of, or in other words, a mutant triplet of DNA may still result in the correct amino acid being placed at the correct position in a protein. This concept is referred to as degeneracy of codons. Alternatively, a degenerate codon synthesized in the context of a short oligonucleotide refers to a mixture of A, C, G or T nucleotides at any position and this tool may be used to introduce genetic diversity at any position. Genetically diverse libraries are typically encoded using NNK or NNS codons, where N=A, G, C or T, K=G or T, and S=C or G different amino acids.

Single-site saturation mutagenesis is a process whereby an individual codon is altered or mutated to any other combinations of A, C, G or T. This process is typically conducted using enzyme-based biochemical reactions or de novo chemical synthesis. With regards to enzyme-based biochemical reactions, a researcher will utilize a degenerate oligonucleotide DNA primer in a polymerase chain reaction (PCR). With this enzyme-based PCR mutagenesis technique, a single set of site-directed mutagenesis oligonucleotides is employed, thus resulting in the enzyme-based PCR mutagenesis technique being limited to a single nucleotide triplet site to be targeted for a given gene. The newly amplified DNA strands will incorporate the genetic diversity encoded by the degenerate codon into the PCR products. With regards to de novo chemical synthesis, a researcher will synthesize new strands of DNA up to the location where saturation mutagenesis is required, at which point they would add in a mixture of A, C, G and T nucleotides to create genetic diversity at the targeted location, having one nucleotide incorporated next in the sequence. By adding in a mixture of nucleotides, genetic diversity is created at that targeted location in newly synthesized DNA strands. Similar to the enzyme-based PCR mutagenesis technique, using de novo chemical synthesis, only a single nucleotide is targetable at once since only a single strand of DNA can be synthesized in a single chemical reaction. Therefore, a major drawback of both the enzyme reaction method and de novo synthesis is that a unique PCR reaction or DNA synthesis reaction is required for every codon that requires saturation mutagenesis thus being limited to targeting a single nucleotide site. Each process must be repeated for each nucleotide base in a gene requiring substitution so as to create a genetically diverse DNA library.

Accordingly, with current and commercially available methods, the single site saturation mutagenesis techniques briefly noted above only facilitate saturation mutagenesis at a single triplet site. Applying a single site saturation mutagenesis technique approach to mutate several DNA positions in a gene is both time consuming and cost ineffective and scaling up these processes to mutagenize multiple codons in a saturated fashion is therefore generally infeasible for both technologies. Consequently, development of a high throughput approach for multi-site saturation DNA mutagenesis would be desirable to facilitate a high throughput method.

Using currently available techniques, the in vitro generation of several mutants using multi-site saturation DNA mutagenesis of a given gene or DNA molecule is not possible in a high throughput manner. Thus, generation of a mutant DNA library, whereby multiple codon sites are mutated for a given gene is cumbersome and time consuming using the currently known and available single-site saturation mutagenesis techniques.

It would be desirable to create a streamlined and cost-effective process for mutagenizing multiple codons in a saturated manner which would serve as an efficient tool for researchers and enable the study of, for example, the consequences of variation or mutation on gene function, human health and drug sensitivity.

This background information is provided to reveal information believed by the applicant to be of possible relevance. No admission is necessarily intended, nor should be construed, that any of the preceding information constitutes prior art.

SUMMARY

The instant disclosure provides a simple molecular cloning technique for multisite saturation mutagenesis. Disclosed herein is technique employing a series of PCR reactions using at least a five-primer PCR approach and biochemical reactions that effectively synthesizes comprehensive genetic diversity along the entire length of a recombinant DNA molecule in vitro. The end product of the herein disclosed technique is a pooled library of synthetic alleles which are amenable for directed evolution, phage display or high-throughput functional experimentation.

The following presents a simplified summary of the general inventive concepts described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

In one aspect there is provided a PCR-based method for generating multi-site saturation mutagenic nucleic acid molecule libraries comprising:
  a) providing a linear double-stranded target template nucleic acid molecule;
  b) providing a first oligonucleotide PCR primer sense to the double-stranded target template nucleic acid molecule and a second oligonucleotide PCR primer antisense to the double-stranded target template nucleic acid molecule, each of the first and second oligonucleotide primers having 5' ends sharing homology with a desired linearized DNA vector and wherein the second oligonucleotide primer is provided as two batches, the first batch having the 5' end of the second oligonucleotide primer harbouring a phosphate moiety so as to provide a phosphorylated second oligonucleotide primer and the second batch being a non-phosphorylated second oligonucleotide primer;
  c) providing a pool containing a plurality of third oligonucleotide primers, each of the third oligonucleotide primers harbouring a 5' phosphate moiety and each having at least one different single triplet site degenerate codon;
  d) conducting a first PCR reaction using the non-phosphorylated second oligonucleotide primer and the plurality of third oligonucleotide primers so as to generate a pool of partial-length mutagenic double-stranded oligonucleotides harbouring mutations introduced from the third oligonucleotide primers and wherein the sense strand is phosphorylated at the 5' end;
  e) conducting a second PCR reaction using the first oligonucleotide primer and the phosphorylated second oligonucleotide primer so as to generate a pool of full-length double-stranded nucleic acid molecules phosphorylated at the 5' end of the antisense strand;
  f) degrading the phosphorylated oligonucleotide strands in the products of steps d) and e) using one or more restriction enzymes; and
  g) recovering from step f) a pool of an antisense single-stranded partial-length mutagenic oligonucleotides and sense single-stranded target template nucleic acid.

In another aspect there is provided a PCR-based method for generating multisite saturation mutagenic nucleic acid molecule libraries comprising:
  a) providing a target template nucleic acid molecule;
  b) providing a first oligonucleotide PCR primer sense to the template nucleic acid molecule and a second oligonucleotide PCR primer antisense harbouring a phosphate moiety so as to provide a phosphorylated second oligonucleotide primer to the target template nucleic acid molecule, each of the first and second oligonucleotide primers having extraneous 5' sequences which are devoid of insertion site homology with a desired suitable cloning vector;
  c) conducting a first PCR reaction using the target template nucleic acid molecule, the first oligonucleotide primer and the phosphorylated second oligonucleotide primer so as to render a pool of full-length double-stranded nucleic acid molecules phosphorylated at the 5' end of the antisense strand and dividing the pool of full-length double-stranded nucleic acid molecules into a first batch comprising a pool of full-length double-stranded nucleic acid molecules and a second batch comprising a pool of full-length double-stranded nucleic acid molecules;
  d) providing a pool containing a plurality of third oligonucleotide primers each of the third oligonucleotide primers harbouring a 5' phosphate moiety and each having at least one different single triplet site degenerate codon and a fourth oligonucleotide primer;
  e) conducting a second PCR reaction using the second batch comprising a pool of full-length double-stranded nucleic acid molecules, the third oligonucleotide primers and the fourth oligonucleotide primer so as to render a pool of partial-length mutagenic double-stranded oligonucleotides harbouring mutations introduced from the third oligonucleotide primers and wherein the sense strand is phosphorylated at the 5' end;
  f) combining the first batch of full-length double-stranded nucleic acid molecules from step c) and the pool of partial-length mutagenic double-stranded oligonucleotides harbouring mutations from step e) and degrading the phosphorylated oligonucleotide strands in the products of steps c) and e) using at least one restriction enzyme; and
  g) recovering from step f) a pool of an antisense single-stranded partial-length mutagenic oligonucleotides and sense single-stranded target template nucleic acid.

In some embodiments, for example, in a first embodiment, disclosed herein, first PCR reaction is run to the early exponential growth phase and the first and second PCR reactions are run in parallel. Whereas in other embodiments, for example the second embodiment disclosed herein, the first and second PCR reactions are run to the early exponential phase.

In some exemplary embodiments, the one or more restriction enzyme is DpnI and/or lambda exonuclease.

In some exemplary embodiments, for example a first disclosed exemplary embodiment, the PCR-based method for generating multisite saturation mutagenic nucleic acid molecule libraries disclosed herein further comprises:
  h) subjecting the pool antisense single-stranded of partial-length mutagenic oligonucleotides and sense single-stranded target template nucleic acid to a third PCR reaction using a fourth oligonucleotide primer and a fifth oligonucleotide primer and wherein the 5' end regions of the fourth and fifth oligonucleotide primers match the 5' end regions of the first and second oligonucleotide primers.

In some exemplary embodiments, for example, in a second disclosed embodiment, the PCR-based method for generating multisite saturation mutagenic nucleic acid molecule libraries disclosed herein further comprises:
  a) subjecting the pool antisense single-stranded of partial-length mutagenic oligonucleotides and sense single-stranded target template nucleic acid to a third PCR reaction using a fifth oligonucleotide primer.

In some embodiments, the third PCR reaction is allowed to proceed until saturation so as to produce a full-length DNA PCR product pool of double-stranded target nucleic acid molecules carrying missense mutations resultant from the pool of plurality of third oligonucleotide primers.

In some embodiments, the PCR-based method for generating multi-site saturation mutagenic nucleic acid molecule libraries further comprises:
  i) recovering the full-length DNA PCR-product carrying missense mutations from step h) and subjecting the full-length DNA PCR-product to gel purification.

In some preferred embodiments, the PCR-based method for generating multisite saturation mutagenic nucleic acid molecule libraries further comprises:

j) selecting a desired size of full-length DNA PCR-product carrying missense mutations from the gel purification of step i).

In some exemplary embodiments, the PCR-based method for generating multisite saturation mutagenic nucleic acid molecule libraries further comprises:

k) inserting and transforming the full-length DNA PCR product carrying missense mutations into the desired suitable cloning vector.

In some exemplary embodiments, the PCR-based method for generating multisite saturation mutagenic nucleic acid molecule libraries further comprises replicating a desired quantity of full-length DNA PCR product carrying missense mutations, once the full-length DNA PCR product carrying missense mutations is inserted and transformed in the desired suitable cloning vector, using a suitable selected bacteria.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

In order that the invention may be better understood, exemplary embodiments will now be described by way of example only, with reference to the accompanying figures, wherein:

FIG. 5 is a sequencing of six representative bacterial transformation clones confirming a single missense mutation in different codon positions for a BRCA1-BRCT library, including the following sequences: SEQ ID NO: 1 (Wildtype BRCA1 sequence (AA1725-AA1784); SEQ ID NO: 2 (Clone A, missense mutation location—AA1782); SEQ ID NO: 3 (Clone B, missense mutation location—AA1768); SEQ ID NO: 4 (Clone C, missense mutation location—AA1726); SEQ ID NO: 5 (Clone E, missense mutation location—AA1782), (note that Clones D and F have no missense mutations and are therefore the same as SEQ ID NO: 1)

DETAILED DESCRIPTION

With reference to the disclosure herein and the appended figures, a method of generating a library of genetically diverse double stranded nucleic acid molecules in accordance with various embodiments of the invention is provided.

In order to generate a mutant DNA library in accordance with the instant disclosure a Gibson assembly approach is employed using a multi-oligonucleotide primer system and a plurality of sequential PCR reactions to create the library of mutant DNA which can then be inserted into a target vector.

Briefly, as would be known by a person of skill in the art, the Gibson assembly approach requires that the 5' ends of the forward and reverse PCR primers are homologous to the cloning insertion site in the linearized vector. The PCR product and the linearized vector DNA are combined. A 5' to 3' exonuclease is used to create single stranded 3' overhangs in the two DNA component strands where the complementary sequences anneal to join the two pieces of DNA. DNA polymerase and A, T, C and G nucleotides then extend the 3' ends to fill in the gaps and DNA ligase seals the remaining nicks. The result is a circular DNA molecule where the PCR product is inserted into the cloning insertion site of the vector.

Figure 1:
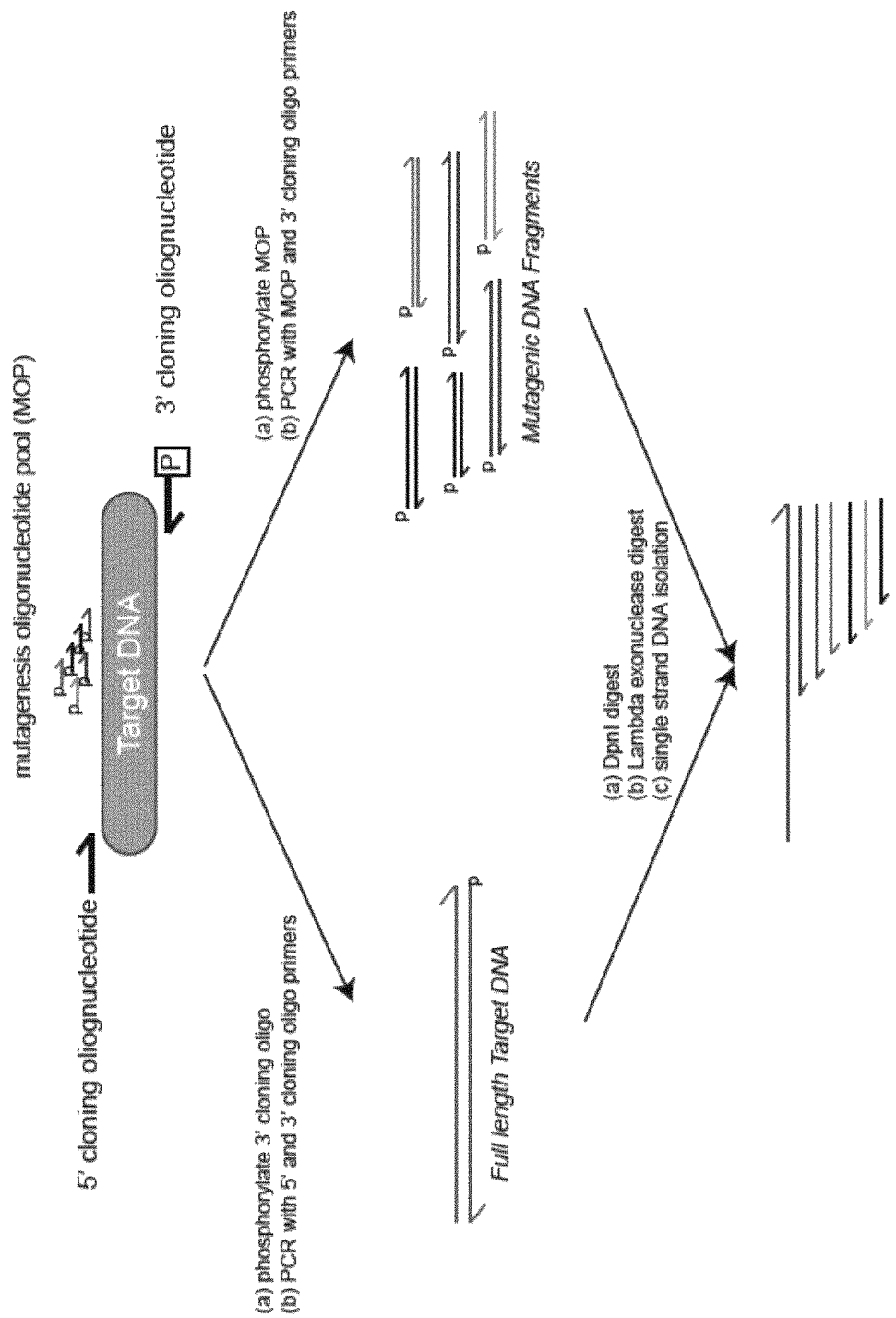
FIG. 1 is a schematic diagram of the three primer PCR reactions of an exemplary embodiment of the instant disclosure to produce an antisense ssDNA (single-stranded DNA) pool of mutagenic oligonucleotides and sense ssDNA template of the gene of interest.

Now, with reference to an embodiment of the technique disclosed herein and with reference to a first exemplary embodiment, as shown, for example in FIG. 1, a first oligonucleotide primer is designed to share homology to one end of the linearized DNA vector at a desired insertion location. The second oligonucleotide is designed to share homology at the opposing end of the linearized DNA vector at a desired insertion location. Therefore the first and second oligonucleotide primers allow for the subsequent Gibson assembly, as noted below. Additionally, the second oligonucleotide primer also has portion thereof phosphorylated so as to produce one batch thereof containing non-phosphorylated second 3' oligonucleotide primer and another batch thereof phosphorylated second 3' oligonucleotide primer, as discussed below.

The third oligonucleotide primer is an oligonucleotide having a single triplet site degenerate codon and is designed sense to the DNA template. In order to create the multi-site saturation mutant DNA library a plurality of said so-called third oligonucleotide primers are prepared, each encoding for desired degenerate codon.

Figure 2:
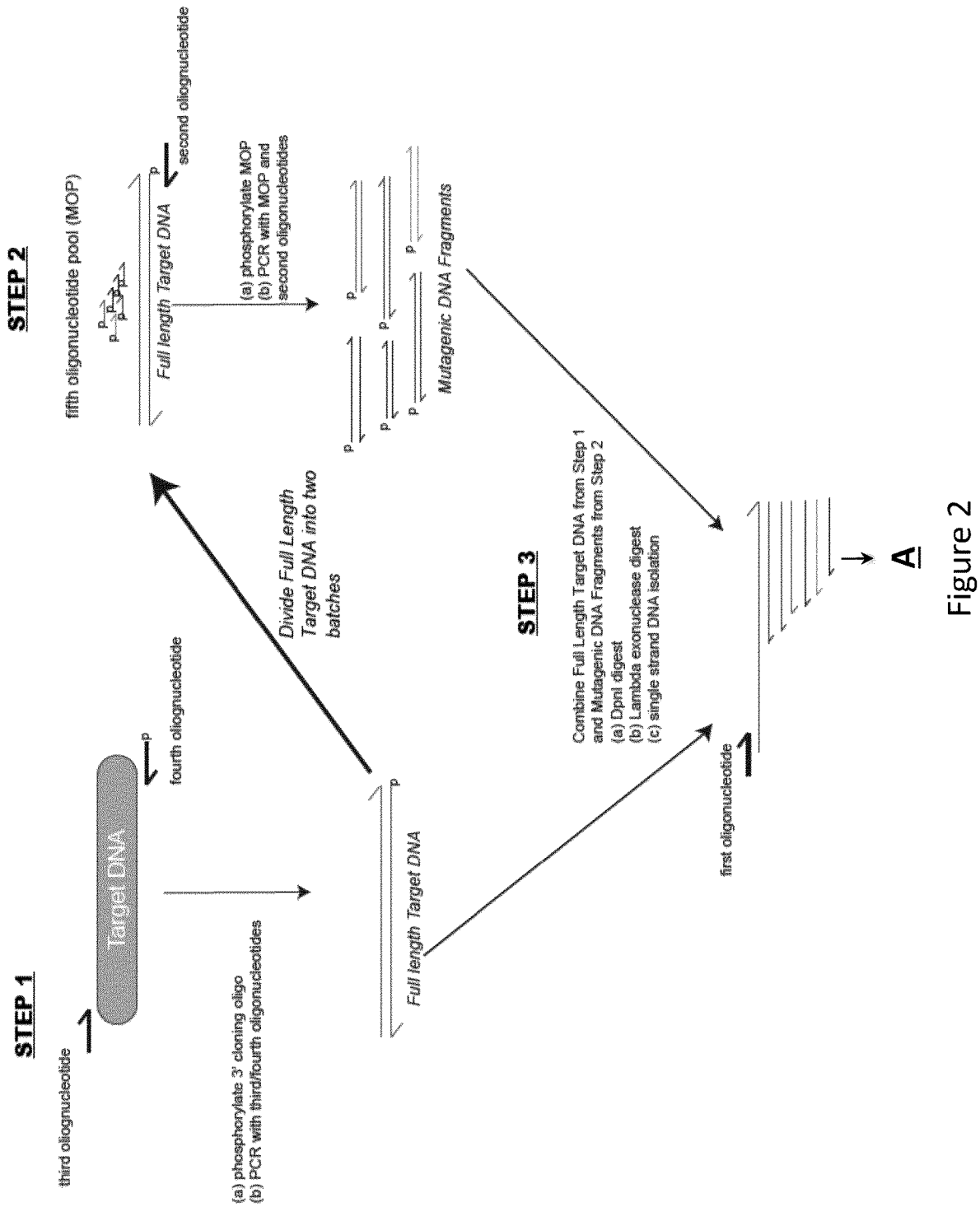
FIG. 2 is a schematic diagram of the five primer PCR reactions of an exemplary embodiment the instant disclosure to produce an antisense ssDNA (single-stranded DNA) pool of mutagenic oligonucleotides and sense ssDNA template of the gene of interest.

Turning now to a second exemplary embodiment of the instantly disclosed technique, as shown, for example with reference to FIG. 2, first and second oligonucleotide primers are designed to not share homology to a suitable cloning vector, for example a linearized DNA vector, at a desired insertion location. Therefore, PCR products using the first and second oligonucleotide primers cannot be subsequently Gibson assembled. However, a fourth oligonucleotide primer is designed to share homology to one end of the linearized DNA vector at a desired insertion location and a fifth oligonucleotide primer is designed to share homology at the opposing end of the linearized DNA vector at a desired insertion location. Therefore, the fourth and fifth oligonucleotide primers allow for the subsequent Gibson assembly, as noted below.

A pool of third oligonucleotides primers is provided wherein the pool comprises plurality of oligonucleotides each having a single triplet site degenerate codon and are designed sense to the DNA template. In order to create the multi-site saturation mutant DNA library a plurality of said so-called third oligonucleotide primers are prepared, each encoding for desired degenerate codon.

Referring to both of the referenced embodiments of the instantly disclosed technique, the plurality of the third primers are then pooled resulting in a multiplex pooled set of third oligonucleotide primers wherein the pool encodes for several desired degenerate codons. Therefore, the multiplex pool of third oligonucleotide primers are termed herein as mutagenesis oligonucleotides and thus each encodes for a single mutagenized codon. Following the concept of a degenerate NNK codon at a desired target position in a desired and given gene, the third oligonucleotide primers are synthesized to each encode for an amino acid substitution at a desired target codon position. Thus, a single oligonucleotide third primer is designed for every codon position in the target gene which is desired to be mutated. This, in some embodiments, is performed in a 96-well plate format and then pooled for use in the subsequent PCR (polymerase chain reaction) reaction, as discussed below.

Once combined, the multiplex pool of third oligonucleotide primers and one of the second 3' oligonucleotide primer batches in the first embodiments and the second 3' oligonucleotide primers in the second embodiments are phosphorylated, using for example, T4 Polynucleotide Kinase so as to produce a phosphorylated pool of third oligonucleotide primers and phosphorylated second 3' oligonucleotide primers, as noted above. The phosphorylation of the multiplex pool of third oligonucleotide primers and the second 3' oligonucleotide primer is provided so as to allow the digestion of the 5' phosphorylated DNA strand, using for example, Lambda Exonuclease, carried out later in the instantly disclosed technique. The first, fourth and fifth 5' oligonucleotide primers are not phosphorylated.

Now, the two disclosed exemplary embodiments will be separable discussed below with reference to either one of FIG. 1 or FIG. 2 corresponding to the first and second disclosed exemplary embodiments, respectively.

With reference to the first exemplarily disclosed embodiment and to FIG. 1, in a first PCR reaction, the second 3' non-phosphorylated oligonucleotide primer and the multiplex pool of phosphorylated third oligonucleotide primers are used to generate partial-length mutagenic oligonucleotides. In a second PCR reaction, conducted independently and in parallel with the first PCR reaction, the first 5' non-phosphorylated oligonucleotide primer and the second 3' phosphorylated oligonucleotide primer are used to generate full length DNA which is phosphorylated on the 5' end of the antisense DNA strand.

Continuing with FIG. 1, following the two-abovementioned PCR reactions, the resultant PCR products are pooled and treated with DpnI restriction enzyme to digest the template DNA, and Lambda exonuclease, so as to digest 5' phosphorylated DNA strands. Following the digestions, the resultant DNA molecules are (i) an antisense ssDNA pool of partial-length mutagenic oligonucleotides, and (ii) sense ssDNA template of the gene of interest.

Turning now to the second disclosed embodiment and with reference to FIG. 2 under "Step 1", in a first PCR reaction, the first 5' non-phosphorylated oligonucleotide primer and the second 3' phosphorylated oligonucleotide primer are used to generate a pool of full length target double-stranded nucleic acid molecules which is phosphorylated on the 5' end of the antisense DNA strand. The resultant full length target double-stranded nucleic acid molecules is then divided into a first batch comprising a pool of full-length double-stranded nucleic acid molecules and a second batch comprising a pool of full-length double-stranded nucleic acid molecules. The pool of full length target double-stranded nucleic acid molecules is divided into the two batches so as to avoid remnant PCR reagent contamination in subsequent PCR reactions, discussed below, as part of the instantly disclosed method.

In a second PCR reaction, conducted subsequently with the second batch comprising a pool of full-length double-stranded nucleic acid molecules, the fourth 3' oligonucleotide primer and the multiplex pool of phosphorylated third oligonucleotide primers are used to generate partial-length mutagenic oligonucleotides. Accordingly, partial-length mutagenic double-stranded oligonucleotides harbouring mutations introduced from the third oligonucleotide primers and wherein the sense strand is phosphorylated at the 5' end are produced as schematically shown in FIG. 1 under "Step 2".

Continuing with FIG. 2, following the two-abovementioned PCR reactions, the resultant PCR products are pooled, under "Step 3", and treated with DpnI restriction enzyme to digest the template DNA, and Lambda exonuclease, so as to digest 5' phosphorylated DNA strands. Following the digestions, the resultant DNA molecules are (i) an antisense ssDNA pool of partial-length mutagenic oligonucleotides, and (ii) sense ssDNA templates of the gene of interest.

Figure 3:
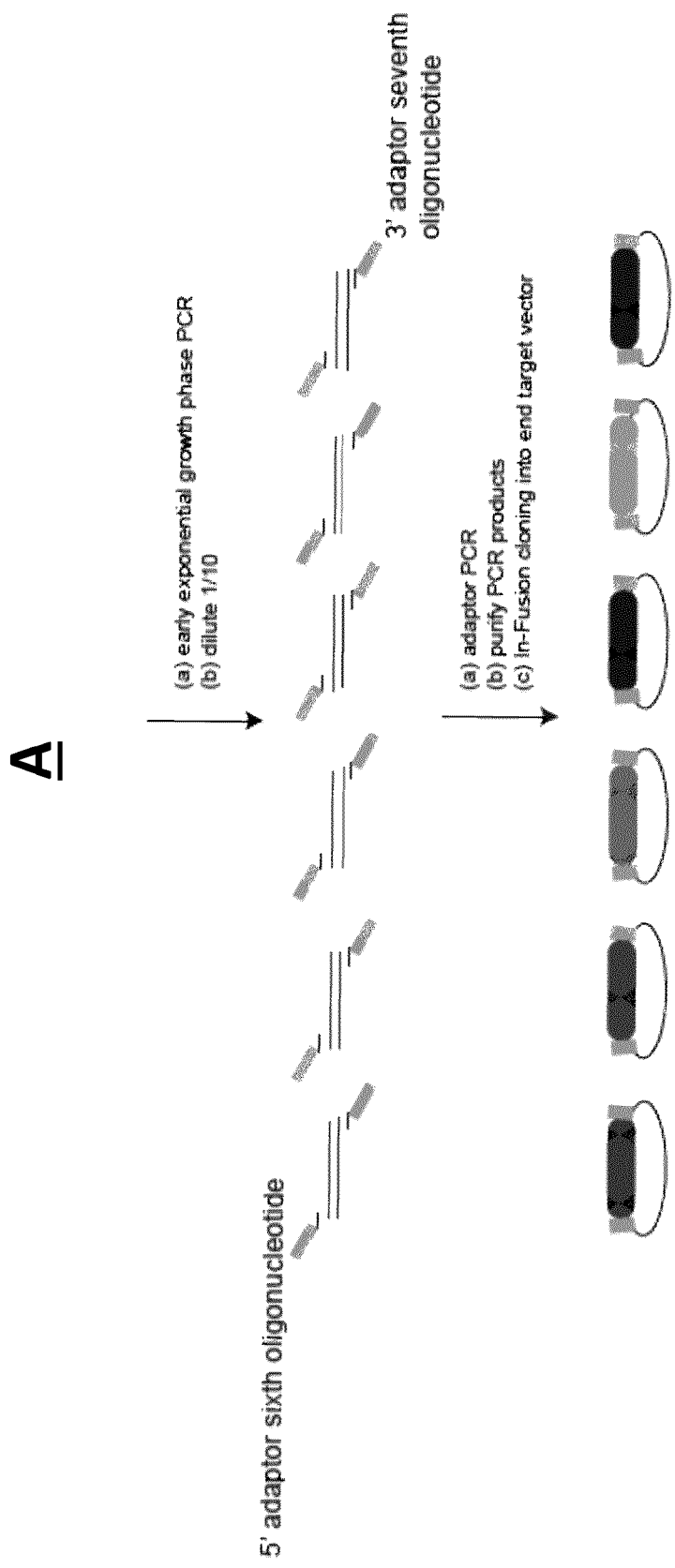
FIG. 3 is a schematic diagram continuing from the antisense ssDNA pool of mutagenic oligonucleotides and the sense ssDNA of FIG. 1 to insert a mutant DNA library of the instant disclosure into a target vector.

Turning now to FIG. 3, a continuance from FIG. 1 (in a first embodiment) and FIG. 2 (in a second embodiment) at A, the (i) an antisense ssDNA pool of partial-length mutagenic oligonucleotides, (ii) sense ssDNA template of the gene of interest and (ii) a fifth oligonucleotide are then combined and a third PCR reaction is undertaken. In this third PCR reaction, the antisense ssDNA pool of partial-length mutagenic oligonucleotides, the sense ssDNA template of the gene of interest, and the fifth oligonucleotide primer are used to generate the library of mutagenic double stranded oligonucleotides. Two additional oligonucleotide primers are designed and further employed in a fourth PCR reaction, termed herein as an enrichment adaptor PCR reaction. These two additional oligonucleotide primers, the sixth and seventh adaptor oligonucleotide primers as shown in FIG. 3, are designed so as to contain nucleotide sequences which match only the 5' region of the fourth and fifth oligonucleotide primers discussed above. The matching 5' end of the sixth and seventh adaptor oligonucleotide primers furthermore share homology with the suitable cloning vector, for example a linearized DNA vector, at a desired insertion location which, once the PCR product of the fourth PCR reaction (enrichment PCR reaction) is purified, allows for the insertion into the cloning vector. Therefore, to insert the produced mutant DNA library into the target vector, the design of the fourth and fifth primers is utilized in the PCR assembly steps. Thus, the resultant library of mutagenic double stranded oligonucleotides contains homology to both ends of the linearized vector. In some embodiments, the resultant purified PCR product from the fourth PCR reaction is inserted into the target vector using In-Fusion cloning (Clontech™). Accordingly, using a Gibson assembly approach, the mutant DNA library is efficiently and precisely cloned into the linearized vector, thereby completing the instantly disclosed high-throughput, multi-site saturation DNA mutagenesis approach.

The above-discussed techniques were validated across different gene sets using two human cDNA templates, BRCA1 and TP53 with results discussed below. The multisite saturation mutagenesis protocol accordingly was conducted on the two human cDNA templates of BRCA1 and TP53, which were cloned into vector DNA as provided below in the example section.

EXAMPLE

Materials and Methods
Plasmid Construction

BRCA1 and TP53 were cloned into pRS425 (XhoI) and pRS413 (EcoRI) plasmids, respectively, at the indicated restriction sites. The cDNA for BRCA1 and TP53 genes were amplified from a human testis cDNA library, using CloneAmp HiFi PCR Premix (Clontech™). The cDNA library was generated using PrimeScript reverse transcriptase (Clontech™), according to the manufacturer's instructions, and human testis polyA+RNA (Clontech™) as the template. Once amplified, the BRCA1 and TP53 genes were cloned into their respective end vectors by In-Fusion cloning (Clontech™) according to the manufacturer's instructions.

Oligonucleotide Design and Synthesis

Mutagenesis oligonucleotides, the above-discussed third oligonucleotide primers, were designed and synthesized in order to mutagenize a single codon in the target gene. By using a degenerate NNK codon at the target codon position, oligonucleotides were synthesized that encode for various possible amino acid substitutions at the target codon position. A single oligonucleotide was designed for every codon position in the target gene and synthesized in a 96-well plate format.

Two cloning oligonucleotides, the fourth and fifth above-discussed oligonucleotide primers, that are complementary to both ends of the target gene for the purposes of PCR-amplification and Gibson assembly were designed and synthesized. In addition to complementarity to the target gene, these oligonucleotides contain sequences at their 5' ends that share homology to the end-target cloning vector, which allows for In-Fusion cloning (Clontech™), as described below.

Two cloning oligonucleotides, the first and second above-discussed oligonucleotide primers, that are complementary to both ends of the target gene for the purposes of PCR-amplification were designed and synthesized. In addition to complementarity to the target gene, these oligonucleotides, the first and second oligonucleotide primers, contain extraneous sequences at their 5' ends which do not share homology to the end-target cloning vector. Accordingly, such extraneous sequences resultant from the first and second oligonucleotide primers, prohibits any PCR products containing such extraneous sequences from incorporation into the end-target cloning vector, for example when utilizing the In-Fusion cloning (Clontech™).

Two adaptor oligonucleotides, the sixth and seventh oligonucleotide primers as discussed above, that only contain sequences matching the 5' region of each cloning oligonucleotide were designed and synthesized. The adaptor oligonucleotides are used in an enrichment PCR reaction, as discussed above and which is further described below.

Oligonucleotide Phosphorylation

The multiplex pool of third oligonucleotide primers and the second 3' oligonucleotide primer were phosphorylated using T4 polynucleotide kinase (T4 PNK) (ThermoFisher Scientific) according to the manufacturer's protocol. Briefly, oligonucleotides at a concentration of 10 micromolar were treated with T4 PNK for one hour at ambient temperature. The reaction was terminated by heat-inactivation of T4 PNK and the phosphorylated oligonucleotides were stored at −20° C. until use.

Polymerase Chain Reactions

All PCR reactions were performed using the CloneAmp HiFi polymerase (Clontech™) according to manufacturer's protocols.

Single Stranded DNA Isolation

The volume of lambda exonuclease treated PCR reactions were adjusted to 100 microlitres using ddH$_2$O. To this mixture, 25 microlitres of 1M Tris-HCl pH 8.0, 25 microlitres of phenol and 50 microlitres of chloroform:isoamyl alcohol (24:1) was added. The resulting aqueous and organic phases were separated using centrifugation (10,000×g, 1 minute). The aqueous phase was extracted and one additional volume of chloroform:isoamyl alcohol was added. The resulting aqueous and organic phases were once again separated using centrifugation (10,000×g, 1 minute). The aqueous phase was extracted and mixed with 1/10 volume of 3 molar Sodium Acetate pH 5.2, 1/20 volume of Glycogen (Thermofisher Scientific) and 3 volumes of 100% ethanol. The sample was then incubated at −20° C. for minimally one hour for DNA precipitation to occur. After incubation, the precipitated DNA was collected by centrifugation (12,000×g, 10 minutes). The supernatant was disposed of and the pellet was air-dried. Lastly, the DNA pellet is resolubilized in ddH$_2$O and the concentration is measured using a NanoDrop spectrophotometer In Fusion Cloning Cloning of purified PCR products into end-target vector was performed using the In-Fusion Cloning Kit (Clontech™).

Results

As shown schematically in FIGS. 1, 2 and 3, a methodology for multi-site saturation mutagenesis of recombinant DNA molecules has been developed in accordance with the instant disclosure. The herein disclosed method was validated using the cDNAs of human BRCA1 and TP53. For BRCA1, a multisite saturation mutagenesis for the C-terminal BRCT domain, which spans codon regions 1640-1863 was conducted. For TP53, similarly, a multisite saturation mutagenesis for the full-length protein, which contains 393 codons was conducted.

The first stage of conducting the multisite saturation mutagenesis is to phosphorylate the mutagenesis oligonucleotides (third oligonucleotide primers) and 3' cloning oligonucleotide (phosphorylated 3' second oligonucleotide primer) using T4 PNK. The 3' cloning oligonucleotide (phosphorylated 3' second oligonucleotide primer) was phosphorylated on its own. The mutagenesis oligonucleotides (third oligonucleotide primers) were phosphorylated in a pooled manner. The multiplex pools of mutagenesis oligonucleotides were made by combining an equal volume of oligonucleotide from each well of the 96-well plate into a single reservoir. Thus, a single pool of mutagenesis oligonucleotides for each 96-well plate was created. For BRCA1-BRCT domain, three mutagenesis oligonucleotide pools were created and for TP53, five mutagenesis oligonucleotide pools were created.

Figure 4B:
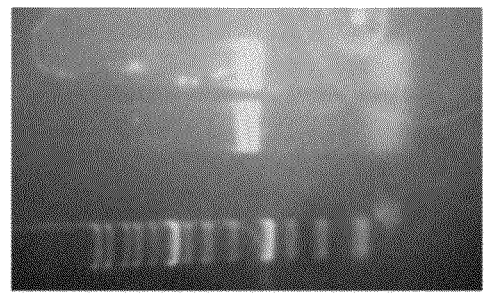
FIG. 4B is a photograph of an agarose gel of PCR product of full-length TP53 in duplicate.
Figure 4A:
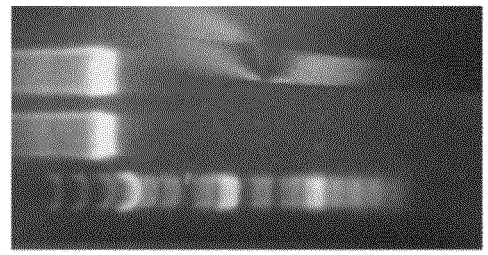
FIG. 4A is a photograph of an agarose gel of PCR product of full-length BCRA1 in duplicate.

The second stage of multisite saturation mutagenesis was to generate single stranded DNA intermediates of the full-length recombinant DNA and partial-length mutagenic DNA fragments. Conducting a PCR reaction using the non-phosphorylated 5' cloning (first 5' oligonucleotide primer) and phosphorylated 3' cloning oligonucleotide (phosphorylated 3' second oligonucleotide primer) set for both genes generated the double stranded, full length BRCA1 and TP53. The DNA templates in each PCR reaction were the respective genes cloned into vector DNA. After conducting a PCR reaction using CloneAmp HiFi polymerase and confirming the presence of the expected DNA product on an agarose gel as shown in FIGS. 4A and 4B, the resultant PCR products were treated with both DpnI (NEB) and lambda exonuclease (ThermoFisher Scientific) and the resulting single stranded DNA molecules were isolated as is shown schematically in FIG. 1.

Figure 4D:
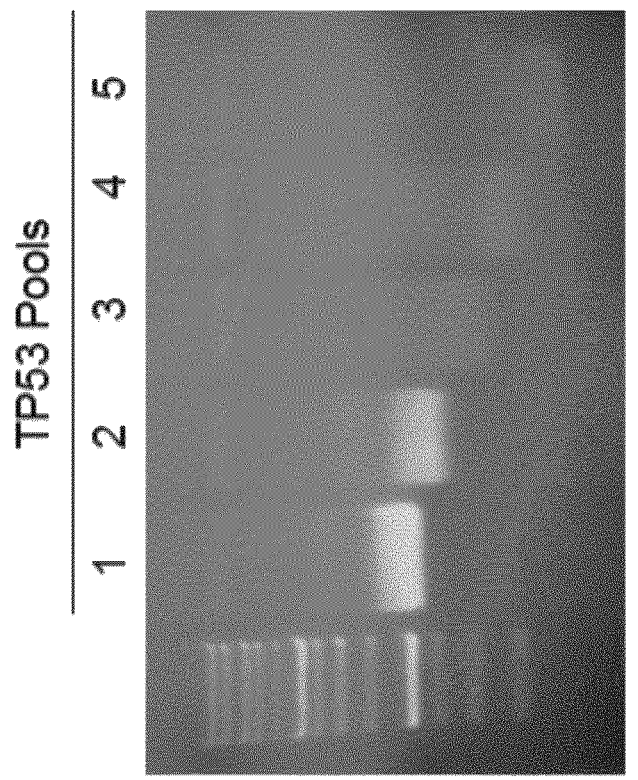
FIG. 4D is a photograph of an agarose gel of PCR product of three pools of mutagenic oligonucleotides for the TP53 gene.
Figure 4C:
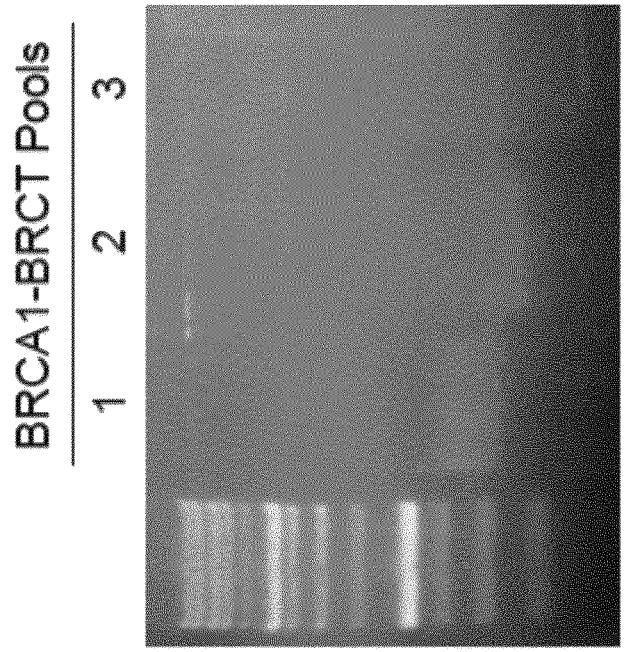
FIG. 4C is a photograph of an agarose gel of PCR product of three pools of mutagenic oligonucleotides for the BCRA-BRCT gene.
Figure 4F:
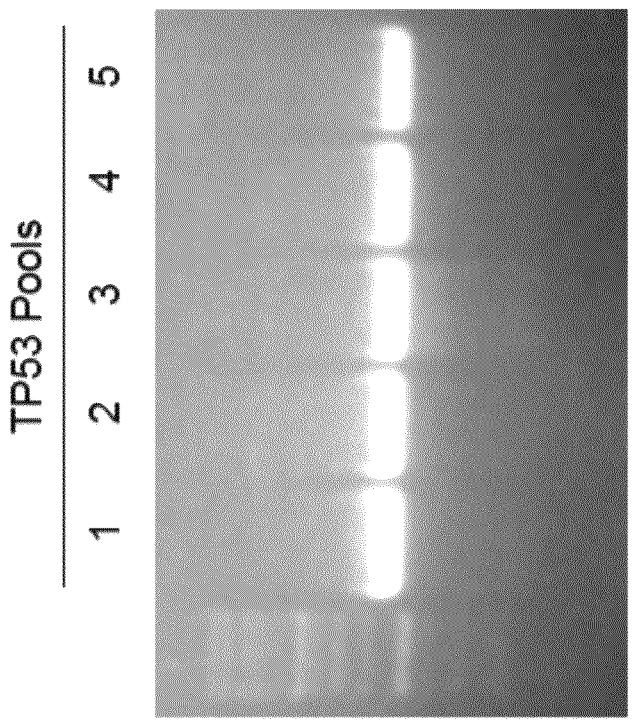
FIG. 4F is a photograph of an agarose gel of adaptor PCR product mutagenic pools for the TP53 gene.
Figure 4E:
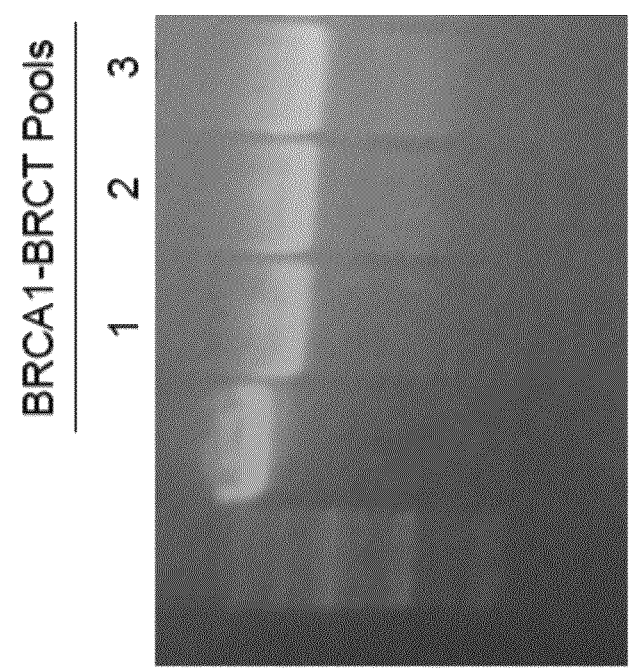
FIG. 4E is a photograph of an agarose gel of adaptor PCR product mutagenic pools for the BCRA-BRCT gene.

A similar protocol is conducted in parallel to generate a pool of antisense strand partial-length mutagenic DNA fragments. Briefly, a multiplex PCR reaction was conducted using the phosphorylated mutagenesis oligonucleotide pool (third oligonucleotide primers) and non-phosphorylated 3' cloning oligonucleotide (non-phosphorylated 3' fourth oligonucleotide primer) as primers. This multiplex PCR reaction was conducted to early exponential growth phase (cycles 12-14) to prevent the incorporation of multiple missense mutations into a single PCR product molecule. A single multiplex PCR reaction was conducted for every mutagenesis oligonucleotide pool. Thus, three multiplex PCR reactions for the BRCA1-BRCT domain and five multiplex PCR reactions for TP53 were performed. Each PCR reaction yielded a laddered DNA product with the expected size range on an agarose gel as shown, for example in FIGS. 4C and 4D. The PCR reaction product was then treated with DpnI (NEB) and lambda exonuclease (ThermoFisher), followed by single stranded DNA isolation. The resulting antisense partial length DNA fragments carry the genetic diversity encoded by the degenerate mutagenic oligonucleotides. Furthermore, these antisense DNA fragments are complementary to the sense full-length recombinant DNA molecule that was generated in parallel.

A library of double stranded BRCA1-BRCT and TP53 mutations was then created using the sense and antisense single stranded DNA intermediate molecules. A mixture of CloneAmp HiFi polymerase with 100 nanograms of 5' cloning oligonucleotide, 10 nanograms of the sense strand full-length recombinant DNA and 250 nanograms of the antisense strand partial-length mutagenic DNA fragments were assembled. Similar to above, a single thermocycle reaction was conducted for each mutagenic pool (three for BRCA1-BRCT and five for TP53). 12 cycles of thermocycling with extended denaturizing and annealing times of one minute were performed. The long denaturation and annealing times aid to yield proper strand annealing and extension.

At the end of 12 cycles, each PCR reaction product was diluted 10-fold using ddH$_2$O and final adaptor enrichment PCR reaction utilizing the adaptor oligonucleotide primers (sixth and seventh oligonucleotide primers) was conducted.

In the adaptor enrichment PCR, the aforementioned diluted PCR reaction product was used as template and the two adaptor oligonucleotide primers (sixth and seventh oligonucleotide primers) were used. This PCR reaction was allowed to proceed until saturation and then resulting full-length DNA product was gel-purified to obtain the correct size product. The results are shown in FIGS. 3E and 3F. This final DNA PCR product is a pool of the target gene carrying unique single missense mutations on each molecule within the pool. Using the In-Fusion cloning kit (Clontech), the DNA fragments were inserted into an end target DNA vector and transformed using the In-Fusion reaction into prepared chemically competent *E. coli* DH5-alpha. 2.5% of the In-Fusion reaction was transformed into fifty microliters of competent bacteria and the number of transformation reactions was scaled to transform the entire In-Fusion ligation reaction. For the BRCA1-BRCT and TP53 libraries, a total of 30 and 50 bacterial transformations, respectively, were conducted.

Figure 5:
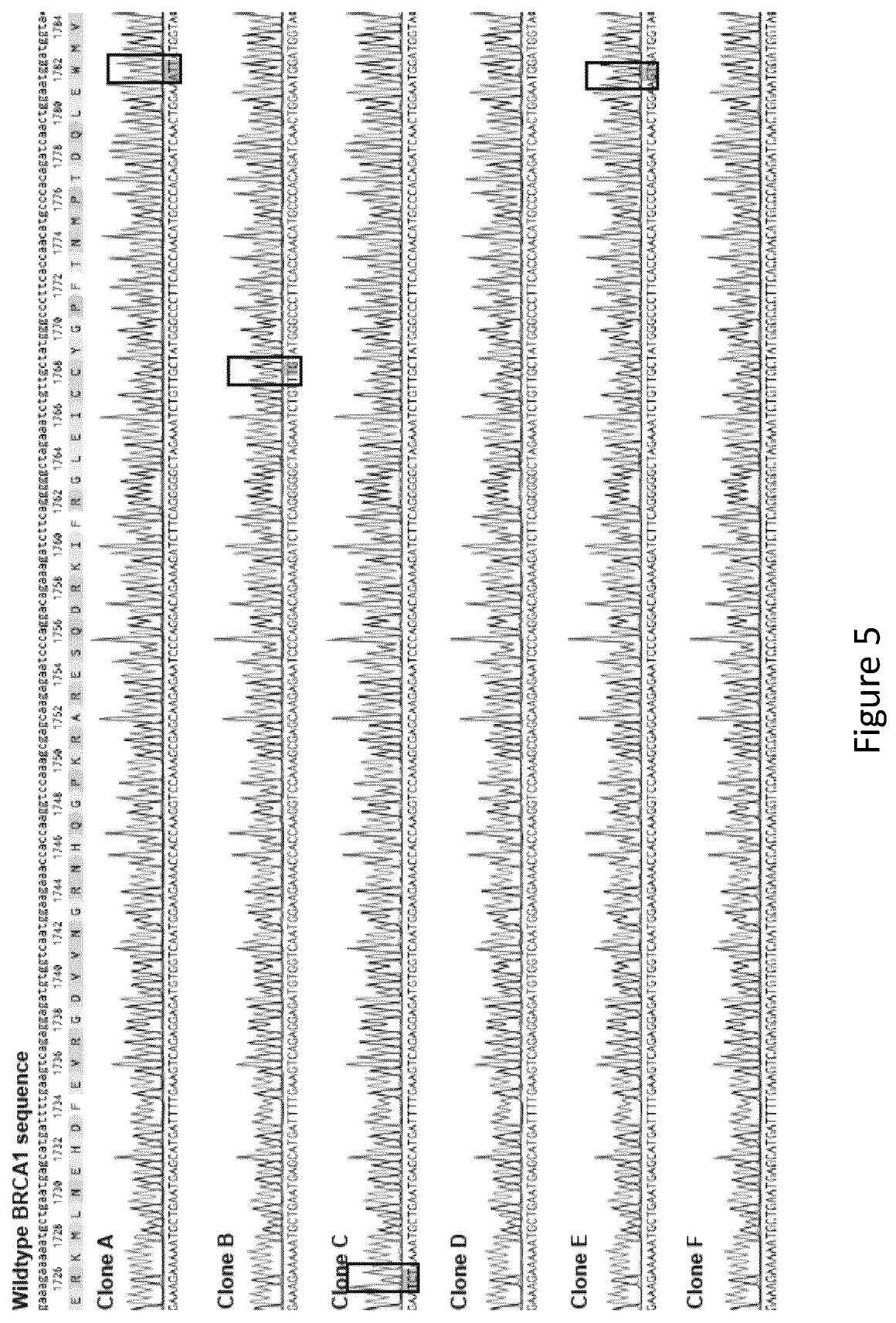
Figure 6:
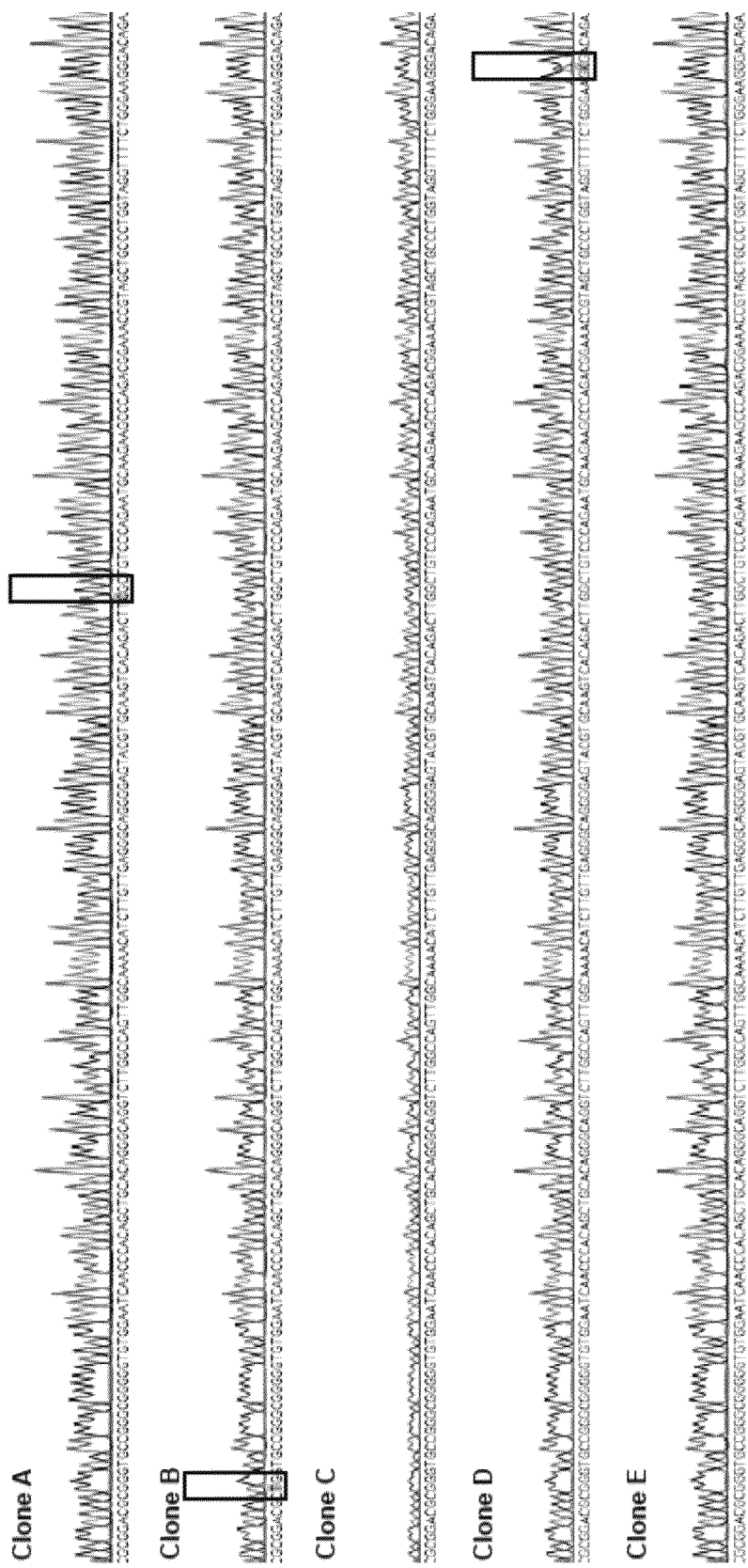
FIG. 6 is a sequencing of five representative bacterial transformation clones confirming a single missense mutation in different codon positions for a TP53 library, including the following sequences: SEQ ID NO: 6 (Wildtype TP53 sequence (AA96-AA158, reverse complement); SEQ ID NO: 7 (Clone A, missense mutation location—AA119); SEQ ID NO: 8 (Clone B, missense mutation location—AA156); SEQ ID NO: 9 (Clone D, missense mutation location—AA98), (note that Clones C and E have no missense mutations and are therefore the same as SEQ ID NO: 6).

In order to validate that the streamlined protocol created genetic diversity along the entire tract of BRCA1-BRCT and TP53, a small volume of each bacterial transformation was plated and sequenced. A selected number of unique colonies is shown in FIG. 5 (BRCA1) and FIG. 6 (TP53). This sequencing confirmed that ~50% of sequenced colonies contained a single missense mutation in different codon positions for both BRCA1-BRCT and TP53 libraries. It was noted that although the remaining non-mutagenized clones were wildtype, the mutagenesis oligonucleotides also encode for wildtype sequences and these oligonucleotides may have a higher propensity to anneal to template DNA in any PCR reaction.

Accordingly, disclosed herein is a novel method for multisite saturation mutagenesis; a means of generating genetic diversity at each desired codon position within the coding sequence of a gene. The instantly disclosed technique may circumvent challenges faced by conventional enzyme-based biochemical reactions and de novo chemical synthesis, which are limited to saturation mutagenesis at single sites. Therefore, the instantly disclosed method for multisite saturation mutagenesis facilitates the efficient synthesis of comprehensive libraries of genetic variants, which may be used to study the effects of genetic mutation/variation.

The instantly disclosed technique may be scaled for multisite saturation mutagenesis high-throughput automation, further improving efficiency and cost-effectiveness.

It is to be understood that the above description it is intended to be illustrative, and not restrictive. Many other embodiments will be apparent to those skilled in the art, upon reviewing the above description. The scope of the invention should, therefore, be determined with reference to the appended claims, along with the full scope of equivalents to which such claims are entitled.

Although the present invention has been described with reference to specific exemplary embodiments, it will be evident that various modifications and changes may be made to these embodiments without departing from the broader spirit and scope of the disclosed subject matter as defined by the appended claims.

What is claimed is:

1. A PCR-based method for generating multisite saturation mutagenic nucleic acid molecule libraries comprising:
   a) providing a linear double-stranded target template nucleic acid molecule;
   b) providing a first oligonucleotide PCR primer sense to said double-stranded target template nucleic acid molecule and a second oligonucleotide PCR primer antisense to said double-stranded target template nucleic acid molecule, each of said first and second oligonucleotide primers having 5' end sharing homology with a desired linearized DNA vector and wherein said second oligonucleotide primer is provided as two batches, the first batch having the 5' end of said second oligonucleotide primer harbouring a phosphate moiety so as to provide a phosphorylated second oligonucleotide primer and the second batch being a non-phosphorylated second oligonucleotide primer;
   c) providing a pool containing a plurality of third oligonucleotide primers, each of said third oligonucleotide primers harbouring a 5' phosphate moiety and each having at least one different single triplet site degenerate codon;
   d) conducting a first PCR reaction using said non-phosphorylated second oligonucleotide primer and said plurality of third oligonucleotide primers so as to generate a pool of partial-length mutagenic double-stranded oligonucleotides harbouring mutations introduced from said third oligonucleotide primers and wherein the sense strand is phosphorylated at the 5' end;
   e) conducting a second PCR reaction using said first oligonucleotide primer and said phosphorylated second oligonucleotide primer so as to generate a pool of full-length double-stranded nucleic acid molecules phosphorylated at the 5' end of the antisense strand;

f) degrading the phosphorylated strands of the products of steps d) and e) using one or more enzymes; and g) recovering from step f) a pool of antisense single-stranded partial-length mutagenic oligonucleotides and sense single-stranded target template nucleic acid.

2. The PCR-based method for generating multisite saturation mutagenic nucleic acid molecule libraries as defined in claim 1, wherein said first PCR reaction is run to the early exponential growth phase.

3. The PCR-based method for generating multisite saturation mutagenic nucleic acid molecule libraries as defined in claim 1, wherein steps d) and e) are conducted in parallel.

4. The PCR-based method for generating multisite saturation mutagenic nucleic acid molecule libraries as defined in claim 2, wherein steps d) and e) are conducted in parallel.

5. The PCR-based method for generating multisite saturation mutagenic nucleic acid molecule libraries as defined in claim 1, wherein the one or more enzymes are DpnI and lambda exonuclease.

6. The PCR-based method for generating multisite saturation mutagenic nucleic acid molecule libraries as defined in claim 1, further comprising:
h) subjecting said pool of antisense single-stranded partial-length mutagenic oligonucleotides and sense single-stranded target template nucleic acid to a third PCR reaction using a fourth oligonucleotide primer and a fifth oligonucleotide primer and wherein the 5' end regions of said fourth and fifth oligonucleotide primers match the 5' end regions of said first and second oligonucleotide primers.

7. The PCR-based method for generating multisite saturation mutagenic nucleic acid molecule libraries as defined in claim 6, wherein said third PCR reaction is allowed to proceed until saturation so as to produce a full-length DNA PCR-product pool of double-stranded target nucleic acid molecules carrying missense mutations resultant from said pool of plurality of third oligonucleotide primers.

8. The PCR-based method for generating multisite saturation mutagenic nucleic acid molecule libraries as defined in claim 7, further comprising:
i) recovering said full-length DNA PCR-product carrying missense mutations from step h) and subjecting said full-length DNA PCR-product to gel purification.

9. The PCR-based method for generating multisite saturation mutagenic nucleic acid molecule libraries as defined in claim 8, further comprising:
j) selecting a desired size of full-length DNA PCR-product carrying missense mutations from said gel purification of step i).

10. The PCR-based method for generating multisite saturation mutagenic nucleic acid molecule libraries as defined in claim 8, further comprising:
k) inserting and transforming said full-length DNA PCR-product carrying missense mutations into a suitable cloning vector.

11. The PCR-based method for generating multisite saturation mutagenic nucleic acid molecule libraries as defined in claim 9, further comprising:
k) inserting and transforming said full-length DNA PCR-product carrying missense mutations into a suitable cloning vector.

12. The PCR-based method for generating multisite saturation mutagenic nucleic acid molecule libraries as defined in claim 10, further comprising: replicating a desired quantity of full-length DNA PCR product carrying missense mutations, once said full-length DNA PCR product carrying missense mutations is inserted and transformed in said suitable cloning vector, using a suitable selected bacteria.

13. The PCR-based method for generating multisite saturation mutagenic nucleic acid molecule libraries as defined in claim 11, further comprising: replicating a desired quantity of full-length DNA PCR product carrying missense mutations, once said full-length DNA PCR product carrying missense mutations is inserted and transformed in said suitable cloning vector, using a suitable selected bacteria.

14. A PCR-based method for generating multisite saturation mutagenic nucleic acid molecule libraries comprising:
a) providing a target template nucleic acid molecule;
b) providing a first oligonucleotide PCR primer sense to the template nucleic acid molecule and a second oligonucleotide PCR primer antisense harbouring a phosphate moiety so as to provide a phosphorylated second oligonucleotide primer to the target template nucleic acid molecule, each of the first and second oligonucleotide primers having extraneous 5' sequences which are devoid of insertion site homology with a desired suitable cloning vector;
c) conducting a first PCR reaction using the target template nucleic acid molecule, the first oligonucleotide primer and the phosphorylated second oligonucleotide primer so as to render a pool of full-length double-stranded nucleic acid molecules phosphorylated at the 5' end of the antisense strand and dividing the pool of full-length double-stranded nucleic acid molecules into a first batch comprising a pool of full-length double-stranded nucleic acid molecules and a second batch comprising a pool of full-length double-stranded nucleic acid molecules;
d) providing a pool containing a plurality of third oligonucleotide primers each of the third oligonucleotide primers harbouring a 5' phosphate moiety and each having at least one different single triplet site degenerate codon and a fourth oligonucleotide primer;
e) conducting a second PCR reaction using the second batch comprising a pool of full-length double-stranded nucleic acid molecules, the third oligonucleotide primers and the fourth oligonucleotide primer so as to render a pool of partial-length mutagenic double-stranded oligonucleotides harbouring mutations introduced from the third oligonucleotide primers and wherein the sense strand is phosphorylated at the 5' end;
f) combining the first batch of full-length double-stranded nucleic acid molecules from step c) and the pool of partial-length mutagenic double-stranded oligonucleotides harbouring mutations from step e) and degrading the phosphorylated strands in the products of steps c) and e) using at least one enzyme; and
g) recovering from step f) a pool of antisense single-stranded partial-length mutagenic oligonucleotides and sense single-stranded target template nucleic acid.

15. The PCR-based method for generating multisite saturation mutagenic nucleic acid molecule libraries as defined in claim 14, wherein said first and second PCR reactions are run to the early exponential growth phase.

16. The PCR-based method for generating multisite saturation mutagenic nucleic acid molecule libraries as defined in claim 14, wherein the at least one enzyme is DpnI and lambda exonuclease.

17. The PCR-based method for generating multisite saturation mutagenic nucleic acid molecule libraries as defined in claim 15, wherein the at least one enzyme is DpnI and lambda exonuclease.

18. The PCR-based method for generating multisite saturation mutagenic nucleic acid molecule libraries as defined in claim 14, further comprising:
   h) subjecting said pool of antisense single-stranded partial-length mutagenic oligonucleotides and sense single-stranded target template nucleic acid to a third PCR reaction using a fifth oligonucleotide primer.

19. The PCR-based method for generating multisite saturation mutagenic nucleic acid molecule libraries as defined in claim 18, wherein said third PCR reaction is allowed to proceed until saturation so as to produce full-length DNA PCR-product pool of double-stranded target nucleic acid molecules carrying missense mutations resultant from said pool of plurality of third oligonucleotide primers.

20. The PCR-based method for generating multisite saturation mutagenic nucleic acid molecule libraries as defined in 18, further comprising:
   i) recovering the full-length DNA PCR-product carrying missense mutations from step h) and subjecting said full-length DNA PCR-product to gel purification.

21. The PCR-based method for generating multisite saturation mutagenic nucleic acid molecule libraries as defined in claim 19, further comprising:
   i) recovering the full-length DNA PCR-product carrying missense mutations from step h) and subjecting said full-length DNA PCR-product to gel purification.

22. The PCR-based method for generating multisite saturation mutagenic nucleic acid molecule libraries as defined in claim 20, further comprising:
   j) selecting a desired size of full-length DNA PCR-product carrying missense mutations from said gel purification of step i).

23. The PCR-based method for generating multisite saturation mutagenic nucleic acid molecule libraries as defined in claim 21, further comprising:
   j) selecting a desired size of full-length DNA PCR-product carrying missense mutations from said gel purification of step i).

24. The PCR-based method for generating multisite saturation mutagenic nucleic acid molecule libraries as defined 20, further comprising:
   k) inserting and transforming said full-length DNA PCR-product carrying missense mutations into the desired suitable cloning vector.

25. The PCR-based method for generating multisite saturation mutagenic nucleic acid molecule libraries as defined in claim 21, further comprising:
   k) inserting and transforming said full-length DNA PCR-product carrying missense mutations into the desired suitable cloning vector.

26. The PCR-based method for generating multisite saturation mutagenic nucleic acid molecule libraries as defined in claim 22, further comprising:
   k) inserting and transforming said full-length DNA PCR-product carrying missense mutations into the desired suitable cloning vector.

27. The PCR-based method for generating multisite saturation mutagenic nucleic acid molecule libraries as defined in claim 23, further comprising:
   k) inserting and transforming said full-length DNA PCR-product carrying missense mutations into the desired suitable cloning vector.

28. The PCR-based method for generating multisite saturation mutagenic nucleic acid molecule libraries as defined in claim 24, further comprising: replicating a desired quantity of full-length DNA PCR product carrying missense mutations, once said full-length DNA PCR product carrying missense mutations is inserted and transformed in said suitable cloning vector, using a suitable selected bacteria.

29. The PCR-based method for generating multisite saturation mutagenic nucleic acid molecule libraries as defined in claim 25, further comprising: replicating a desired quantity of full-length DNA PCR product carrying missense mutations, once said full-length DNA PCR product carrying missense mutations is inserted and transformed in said suitable cloning vector, using a suitable selected bacteria.

30. The PCR-based method for generating multisite saturation mutagenic nucleic acid molecule libraries as defined in claim 26, further comprising: replicating a desired quantity of full-length DNA PCR product carrying missense mutations, once said full-length DNA PCR product carrying missense mutations is inserted and transformed in said suitable cloning vector, using a suitable selected bacteria.

31. The PCR-based method for generating multisite saturation mutagenic nucleic acid molecule libraries as defined in claim 27, further comprising: replicating a desired quantity of full-length DNA PCR product carrying missense mutations, once said full-length DNA PCR product carrying missense mutations is inserted and transformed in said suitable cloning vector, using a suitable selected bacteria.

* * * * *

SEQUENCE LISTING

<160> NUMBER OF SEQ ID NOS: 9

<210> SEQ ID NO 1
<211> LENGTH: 180
<212> TYPE: DNA
<213> ORGANISM: Homo sapiens

<400> SEQUENCE: 1
gaaagaaaaa tgctgaatga gcatgatttt gaagtcagag gagatgtggt caatggaaga      60
aaccaccaag gtccaaagcg agcaagagaa tcccaggaca gaaagatctt caggggcta     120 gaaatctgtt gctatgggcc cttcaccaac atgcccacag atcaactgga atggatggta    180

<210> SEQ ID NO 2
<211> LENGTH: 180
<212> TYPE: DNA
<213> ORGANISM: Homo sapiens

<400> SEQUENCE: 2
gaaagaaaaa tgctgaatga gcatgatttt gaagtcagag gagatgtggt caatggaaga      60
aaccaccaag gtccaaagcg agcaagagaa tcccaggaca gaaagatctt caggggcta     120 gaaatctgtt gctatgggcc cttcaccaac atgcccacag atcaactgga aattatggta    180

<210> SEQ ID NO 3
<211> LENGTH: 180
<212> TYPE: DNA
<213> ORGANISM: Homo sapiens

<400> SEQUENCE: 3
gaaagaaaaa tgctgaatga gcatgatttt gaagtcagag gagatgtggt caatggaaga      60
aaccaccaag gtccaaagcg agcaagagaa tcccaggaca gaaagatctt caggggcta     120 gaaatctgtt tgtatgggcc cttcaccaac atgcccacag atcaactgga atggatggta    180

<210> SEQ ID NO 4
<211> LENGTH: 180
<212> TYPE: DNA
<213> ORGANISM: Homo sapiens

<400> SEQUENCE: 4
gaatctaaaa tgctgaatga gcatgatttt gaagtcagag gagatgtggt caatggaaga      60
aaccaccaag gtccaaagcg agcaagagaa tcccaggaca gaaagatctt caggggcta     120 gaaatctgtt gctatgggcc cttcaccaac atgcccacag atcaactgga atggatggta    180

<210> SEQ ID NO 5
<211> LENGTH: 180
<212> TYPE: DNA
<213> ORGANISM: Homo sapiens

<400> SEQUENCE: 5
gaaagaaaaa tgctgaatga gcatgatttt gaagtcagag gagatgtggt caatggaaga      60
aaccaccaag gtccaaagcg agcaagagaa tcccaggaca gaaagatctt caggggcta     120 gaaatctgtt gctatgggcc cttcaccaac atgcccacag atcaactgga agtgatggta    180

<210> SEQ ID NO 6
<211> LENGTH: 189
<212> TYPE: DNA
<213> ORGANISM: Homo sapiens

<400> SEQUENCE: 6

```
gcggacgcgg gtgccgggcg ggggtgtgga atcaacccac agctgcacag ggcaggtctt    60
ggccagttgg caaaacatct tgttgagggc aggggagtac gtgcaagtca cagacttggc   120
tgtcccagaa tgcaagaagc ccagacggaa accgtagctg ccctggtagg ttttctggga   180
agggacaga                                                           189

<210> SEQ ID NO 7
<211> LENGTH: 189
<212> TYPE: DNA
<213> ORGANISM: Homo sapiens

<400> SEQUENCE: 7
gcggacgcgg gtgccgggcg ggggtgtgga atcaacccac agctgcacag ggcaggtctt    60
ggccagttgg caaaacatct tgttgagggc aggggagtac gtgcaagtca cagacttcgc   120
tgtcccagaa tgcaagaagc ccagacggaa accgtagctg ccctggtagg ttttctggga   180
agggacaga                                                           189

<210> SEQ ID NO 8
<211> LENGTH: 189
<212> TYPE: DNA
<213> ORGANISM: Homo sapiens

<400> SEQUENCE: 8
gcggacgctg gtgccgggcg ggggtgtgga atcaacccac agctgcacag ggcaggtctt    60
ggccagttgg caaaacatct tgttgagggc aggggagtac gtgcaagtca cagacttggc   120
tgtcccagaa tgcaagaagc ccagacggaa accgtagctg ccctggtagg ttttctggga   180
agggacaga                                                           189

<210> SEQ ID NO 9
<211> LENGTH: 189
<212> TYPE: DNA
<213> ORGANISM: Homo sapiens

<400> SEQUENCE: 9
gcggacgcgg gtgccgggcg ggggtgtgga atcaacccac agctgcacag ggcaggtctt    60
ggccagttgg caaaacatct tgttgagggc aggggagtac gtgcaagtca cagacttggc   120
tgtcccagaa tgcaagaagc ccagacggaa accgtagctg ccctggtagg ttttctggga   180
agagacaga                                                           189
```